(12) United States Patent
Henderson et al.

(10) Patent No.: US 7,403,330 B2
(45) Date of Patent: Jul. 22, 2008

(54) SLIDE HOLDER FOR AN AUTOMATED SLIDE LOADER

(75) Inventors: Chester John Henderson, Collingwood (AU); Stephen Collings Morris, Boronia (AU); Ian Donald Reilly, Mt. Waverley (AU); Eduardo Vom, Brunswick East (AU)

(73) Assignee: Leica Biosystems Melbourne Pty Ltd, Mount Waverly, Victoria (AU)

( * ) Notice: Subject to any disclaimer, the term of this patent is extended or adjusted under 35 U.S.C. 154(b) by 46 days.

(21) Appl. No.: 10/471,208

(22) PCT Filed: Mar. 15, 2002

(86) PCT No.: PCT/AU02/00301

§ 371 (c)(1),
(2), (4) Date: Jan. 30, 2004

(87) PCT Pub. No.: WO02/062410

PCT Pub. Date: Aug. 15, 2002

(65) Prior Publication Data

US 2004/0114227 A1    Jun. 17, 2004

(30) Foreign Application Priority Data

Mar. 15, 2001    (AU)    .................................... PR 3761

(51) Int. Cl.
*G02B 21/26* (2006.01)
*G01N 21/01* (2006.01)
(52) U.S. Cl. ........................ 359/391; 359/393; 414/331
(58) Field of Classification Search ......... 359/368–398; 422/63–67; 414/416–431
See application file for complete search history.

(56) References Cited

U.S. PATENT DOCUMENTS 4,159,875 A    7/1979    Hauser ....................... 359/393

(Continued)

FOREIGN PATENT DOCUMENTS

DD    247528 A1    4/1986

(Continued)

OTHER PUBLICATIONS

English Abstract of the Germany reference No. DD 247 528 A1.

(Continued)

*Primary Examiner*—Thong Nguyen
(74) *Attorney, Agent, or Firm*—Shook, Hardy & Bacon, L.L.P.

(57) ABSTRACT

A slide holder (6) for use with a microscope to accurately locate a slide (19) in position under the microscope has a pivotal lever (13) having a clamping and locating portion (14) with abutments (15) and (16) which bear on respective edges of the slide when it is in the clamped position. Further abutments (10) on a fixed angular plate (9) locate the other edges of the slide. The slide holder is adapted for mounting on a slide translation stage of a slide loader (1) which includes a stationary sensor block (20) positioned to engage the lever (13) when the slide holder moves from its inspection or scanning position under the microscope to a loading/unloading position. The slide translation stage includes a robotic head for lifting and depositing slides and the translation stage includes a bar code reader to read a bar code on the slide.

6 Claims, 3 Drawing Sheets

U.S. PATENT DOCUMENTS

| | | | | |
|---|---|---|---|---|
| 4,367,915 A | * | 1/1983 | Georges | 359/385 |
| 4,453,807 A | | 6/1984 | Faulkner et al. | 359/391 |
| 4,807,984 A | | 2/1989 | Kurimura et al. | 359/393 |
| 4,818,169 A | * | 4/1989 | Schram et al. | 414/331.18 |
| 5,000,554 A | | 3/1991 | Gibbs | 359/393 |
| 5,646,776 A | * | 7/1997 | Bacchi et al. | 359/393 |
| 5,659,421 A | | 8/1997 | Rahmel et al. | 359/391 |
| 5,690,892 A | * | 11/1997 | Babler et al. | 422/63 |
| 6,405,610 B1 | * | 6/2002 | Komatsu et al. | 73/865.9 |
| 6,847,481 B1 | * | 1/2005 | Ludl et al. | 359/391 |

FOREIGN PATENT DOCUMENTS

| | | |
|---|---|---|
| DE | 3505334 A1 | 10/1985 |
| JP | 10-039231 | 2/1998 |
| JP | 11-083687 | 3/1999 |
| WO | WO 97/04347 | 2/1997 |

OTHER PUBLICATIONS

English Abstract of the Germany reference No. DE 3505334 A1.
English Abstract of the Japanese reference No. 10-39231.

* cited by examiner

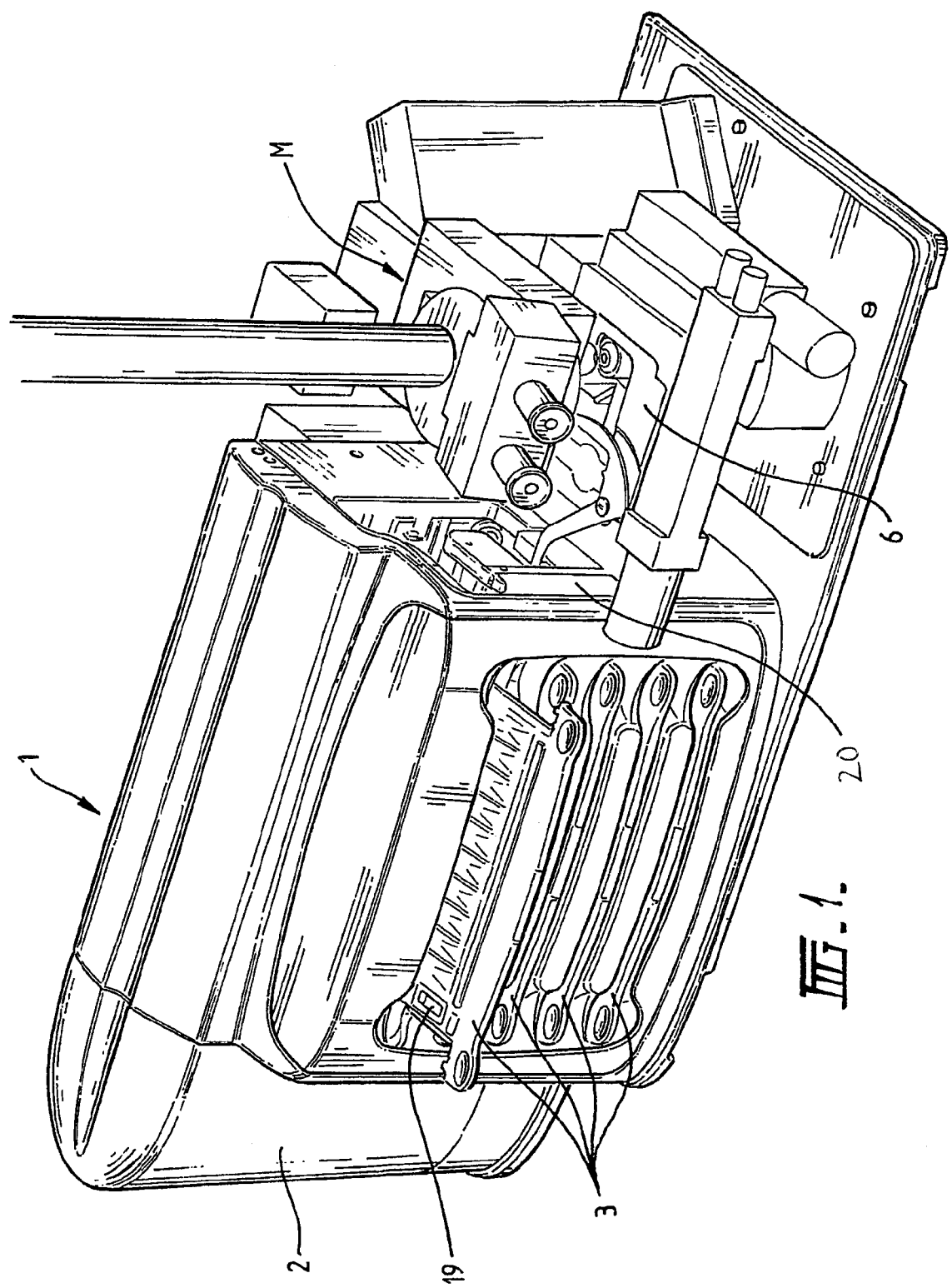

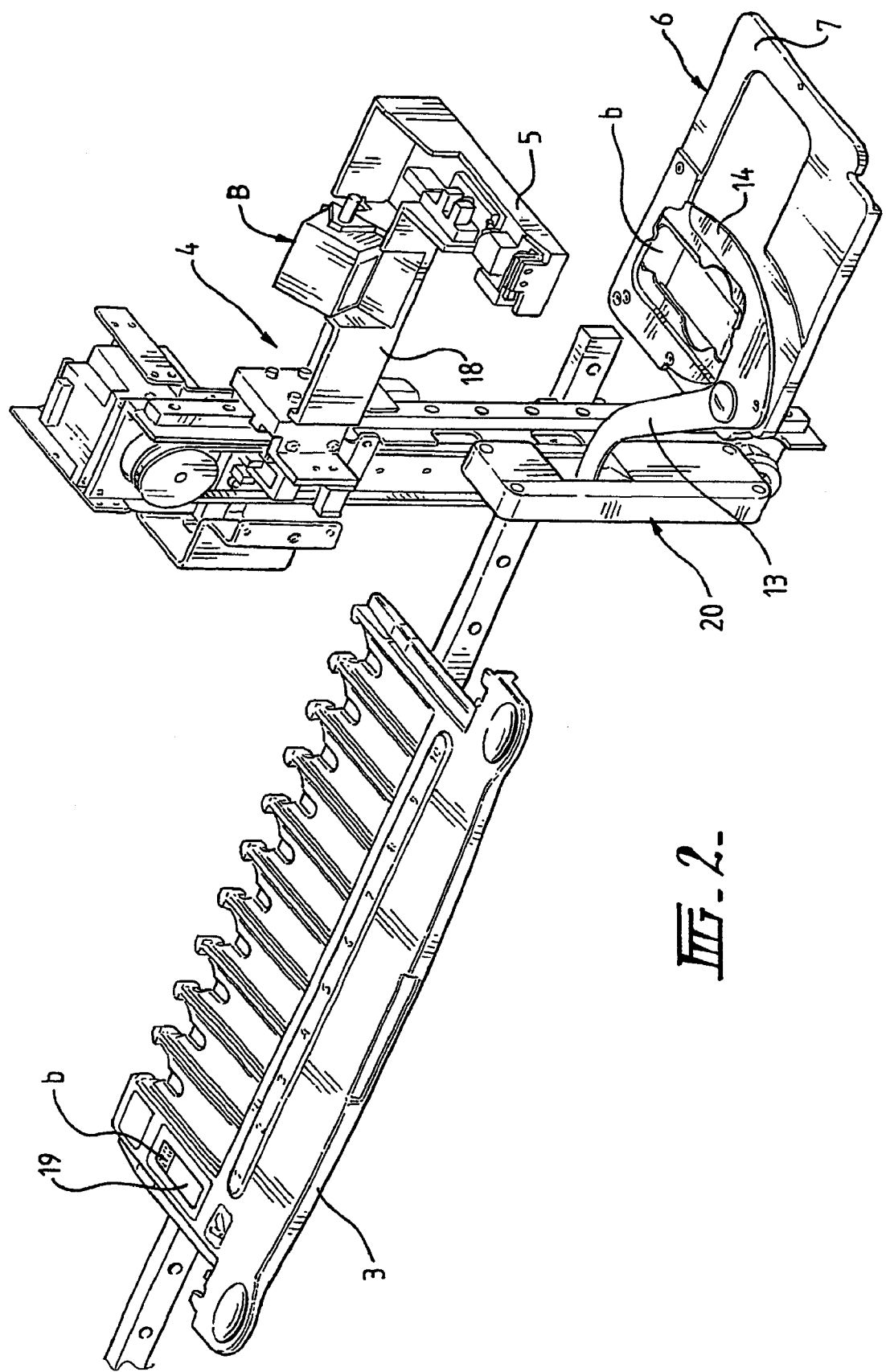

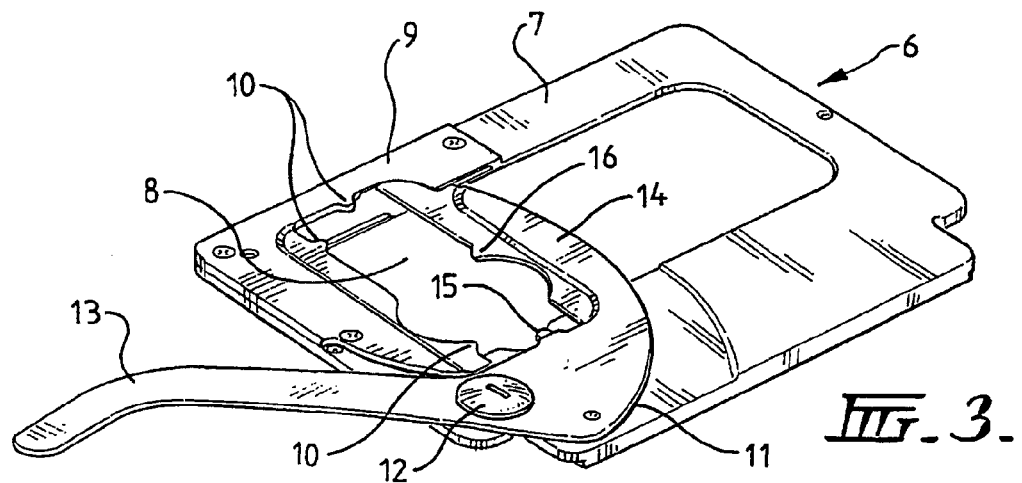
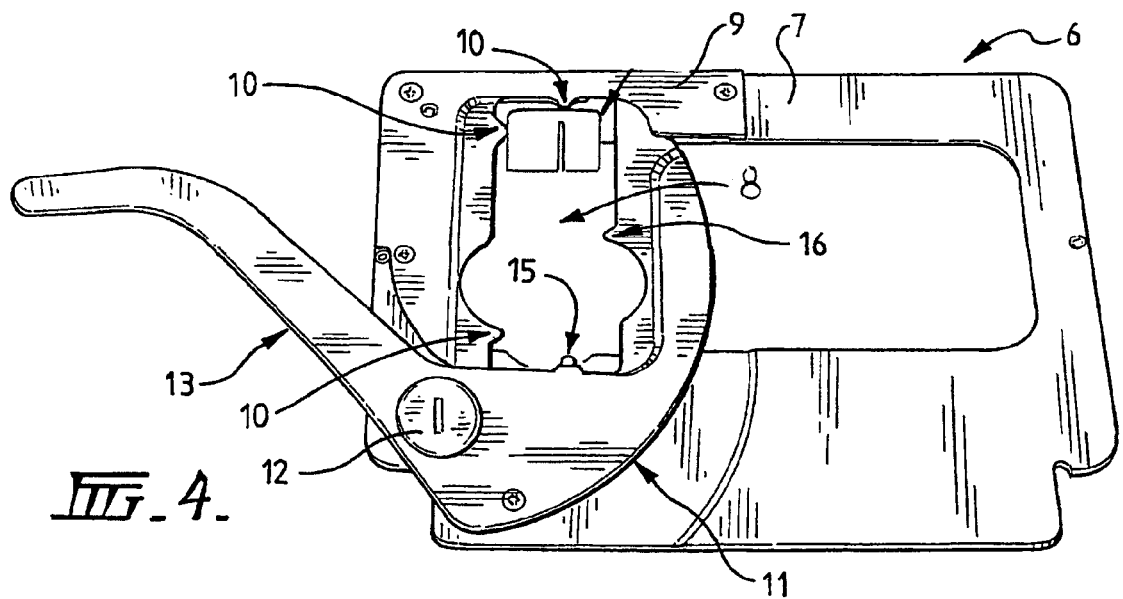
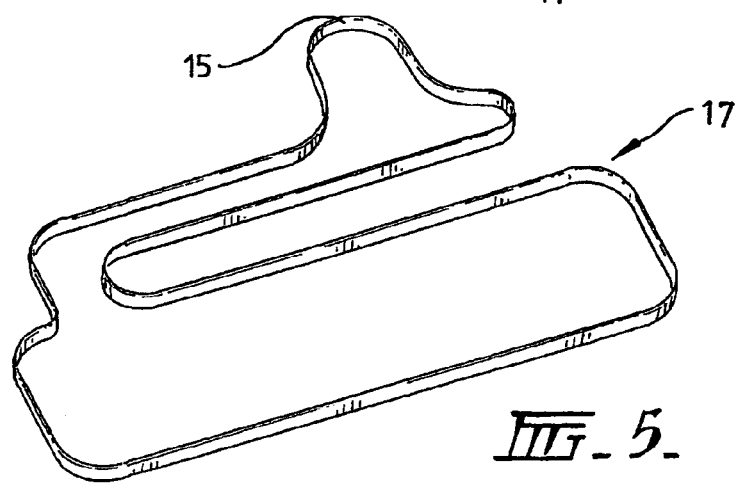

SLIDE HOLDER FOR AN AUTOMATED SLIDE LOADER

FIELD OF THE INVENTION

This invention relates to slide holders for use with an automated slide loader.

BACKGROUND OF THE INVENTION

In recent years there has been a rapid growth in the reported use of automated image processing systems to analyse images obtained from video and digital cameras mounted on optical microscopes. However, the benefits of using such systems have been offset by the need to manually load and unload microscope slides on the microscope.

There is no stand-alone automated slide loader in the market that loads and unloads slides to and from an external, free-standing optical microscope. Current processes of loading and unloading slides are either performed manually or require a dedicated instrument that already has a built-in microscope and imaging system.

There are several patents that describe systems to automatically load and unload slides onto microscopes including U.S. Pat. No. 4,248,498 (Georges), and U.S. Pat. No. 4,501,495 (Faulkner). These patents describe systems whereby the slide loader is integrated into a microscope/imaging platform. It is not possible with these designs to interface to free-standing microscopes.

Slide holders on current model microscopes typically consist of a spring loaded pivot arm to position and clamp slides onto the slide holder. One form of slide holder disclosed is U.S. Pat. 4,159,875 (Hauser). The shortcomings of such holders include:

a) they are limited to manual operation only. They require the user to manually open the clamping mechanism, accurately position the slide on the slide holder, and then release the clamping mechanism. Consequently, such methods are not suited to automated scanning systems as they require constant attendance from laboratory staff to load and unload slides.

b) the positional accuracy achieved by manually locating slides is not always guaranteed.

The use of vacuum chucks as an alternative means to clamp slides on microscope stages have been described in U.S. Pat. No. 4,508,435 (Graham) and U.S. Pat. No. 4,981,345 (Berry). These chucks can accommodate X and Y motion of the stage by the use of flexible vacuum connections but have the following shortcomings:

a) positional accuracy of the slide under the microscope is not guaranteed either by manual or robotic positioning;

b) considerable modifications to a microscope stage are required to accommodate vacuum lines (a vacuum pump is also required but can be mounted away from the microscope).

c) to obtain adequate clamping (suction) of a slide, both ends of the slide would require vacuum thereby reducing the effective scan area on the slides. Therefore critical features on the slide may be missed.

d) Vacuum chucks and associated plumbing can obstruct the optical path between a microscope's condenser and objective lens.

U.S. Pat. No. 4,012,111 describes a slide holder that requires the user to position the slide by hand and push to clamp the slide down. It claims to be able to position slides accurately and repeatedly. The shortcomings of this holder are:

a) the slide holder can only be used manually as it request the user to manually place the slide against one slide retainer before the slide could be clamped down.

b) the slide holder requires a user to use two hands to position a slide correctly; one hand to hold the slide against the fixed locaters on the back and the slide retainer, and the other hand to clamp the slide. It is not designed to automatically locate the slide.

c) the positional accuracy in the x-y plane is dependent on human placement of the slide.

d) the positive force required to clamp the slide into position may lead to crack and chipping of slides.

SUMMARY OF THE INVENTION AND OBJECT

It is an object of the present invention to provide a slide holder for use with an automated slide loader for a microscope in which the short comings of the known slide holders and slide loaders are ameliorated.

The invention thus provides a slide holder for use with a microscope, characterised in that said holder comprises a slide receiving region having a plurality of fixed slide locaters, a slide locating and clamping means movably mounted on the slide holder and including a further plurality of slide locaters for engaging the slide and moving it into positive engagement with the fixed locaters whereby the slide is accurately located and clamped in a fixed position on the holder.

By using the defined combination of fixed locaters and movable locating and clamping means, the slide does not need to be initially placed on the slide holder with any great accuracy since movement of the locating and clamping means ensures that the slide is always accurately positioned against the fixed locaters as the slide is clamped.

The fixed locaters and the locaters on the slide locating and clamping means preferably engage only the edge regions, and preferably only the edges, of the slide to thereby maximise the scan area capable of being viewed by the microscope during examination of each slide.

In a preferred form of the invention, the movable locating and clamping means includes an arm pivoted to the slide holder for movement between an open slide loading position and a closed slide locating and clamping position, said arm preferably having an extended lever portion which may be manually or mechanically engaged to move the arm to the open position, and biasing means for moving the arm to the locating and clamping position when the lever means is released.

The slide holder is preferably configured to be supported by a motorised translation stage associated with a microscope. Such motorised translation stages are known in the art and operate to move the slide holder from a load/unload position to a microscope viewing position in which the slide is appropriately positioned under the microscope. In such an arrangement, the lever means defined above is positioned to engage a stationary sensor block to pivot the arm from the locating and clamped position to the open position as the motorised translation stage moves towards the load/unload position.

It will be appreciated from the above that the slide holder lends itself for use with an automated slide loader adapted to lift slides from a slide tray and deposit the slides onto the slide holder when it is in its load/unload position and the clamping and locating arm is open.

In a further aspect the invention provides a slide holder adapted for mounting on the slide translation stage of a microscope, said slide holder having a slide clamping and/or locating means having an open or loading position and a closed position, and means for moving the clamping/locating means from one position to the other as the slide holder is moved by the translation stage to and from the loading position.

This facility enables the microscope to be used with an automated slide loader, such as that defined further below.

In another aspect, the invention provides a slide loader for use with a microscope fitted with a motorised translation stage, including transfer means for lifting slides from a slide tray or the like, slide holder means adapted for mounting on said motorised translation stage for movement from a slide loading/unloading position to a slide inspection or scanning position under said microscope, said transfer means being adapted to position the lifted slide on the slide holder means, and to lift the slide from the slide holder means after inspection/scanning, said slide holder means including means operative to clamp a slide positioned on the slide holder means during movement of the translation stage from the loading/unloading position to the inspection/scanning position, and for releasing the clamping means when the slide holder returns to the loading/unloading position.

In a preferred form of the invention, the slide holder means is as defined in relation to the first aspect of the invention, the slide loader preferably including means for engaging the lever means as the slide holder is moved by the translation stage towards the loading/unloading position.

The transfer means of the slide loader preferably includes a robotic head member including means for lifting and depositing slides, said transfer means being mounted for independent horizontal and vertical movement during slide transfer from a slide tray or the like to the slide holder.

The slide loader preferably includes a bar code reader adapted to read a bar code applied to said slide thereby enabling the slide loader system to identify and track the slide to be inspected.

BRIEF DESCRIPTION OF THE DRAWINGS

In order that the invention may be more readily understood, a preferred embodiment of each of the above aspects of the invention will now be described with reference to the accompanying drawings in which:

FIG. 1 is a perspective view of a slide loader embodying the invention positioned adjacent a microscope arrangement incorporating a motorised translation stage;

FIG. 2 is a schematic perspective view, on an enlarged scale, of the slide loader and slide holder embodying the invention showing the essential components thereof and an opening for the microscope assembly;

FIG. 3 is a perspective view of the slide holder embodying the invention;

FIG. 4 is similar to FIG. 3 but shows a slide in position on the slide holder; and FIG. 5 is an enlarged perspective view of a spring locating component of the slide holder of FIGS. 3 and 4.

DESCRIPTION OF PREFERRED EMBODIMENTS

Referring firstly to FIGS. 1 and 2 of the drawings, the slide loader 1 includes a housing 2 within which a multiplicity of slide supporting trays 3 are located in a vertical stack. A slide transfer means 4 (FIG. 2) includes a robot head 5 incorporating a suction cup (not shown) with an associated vacuum supply which enables automated lifting of slides 19 from a selected tray 3 followed by depositing of the slides on a slide loader 6 carried by a motorised translation stage of a microscope assembly M. The transfer means 4 is mounted within the slide loader 1 for independent horizontal and vertical movement which enables the robot head to be automatically moved in response to a command from an external controller (not shown) to select a designated slide from one of the trays 3 for loading onto the slide holder 6. An arm 18 supporting the robot head 5 also supports a barcode reader B which operates to read a barcode area b on each slide as it is picked up and returned to the tray 3 by the robot head 5 to ensure that the slides are appropriately monitored and validated.

Referring now to FIGS. 3, 4 and 5 of the drawings, the slide holder 6 includes a frame 7 including a slide location region 8 surrounded on two sides by a shaped angular plate 9 incorporating three fixed slide locating abutments 10. A pivotable arm 11 is mounted on the slide holder frame 7 by a pivot pin 12 engaging the frame 7. The arm 11 has an extended lever portion 13 and a clamping portion 14 having slide engaging abutments 15 and 16, the abutment 15 forming part of a deformable spring component 17, as illustrated in FIG. 5 of the drawings, by means of which the slide holder can compensate for slides of varying sizes. The locating and clamping arm 11 has an associated biasing means (not shown) by means of which the arm is biased towards the closed position, as illustrated in FIGS. 3 and 4, whenever the lever 13 is not held in the open position ready for a slide to be dropped onto the holder 6.

Referring again to FIGS. 1 and 2 of the drawings, it will be noted that the slide loader 1 includes a stationary sensor block 20 positioned to engage the lever 13 of the slide holder 6 when the motorised translation stage of the microscope M moves the slide holder 6 from its inspection or scanning position under the microscope M to the loading/unloading position. This engagement pivots the arm 11 and moves the clamping and locating portion 14 to the open position to enable an existing slide to be removed or a new slide to be deposited. As soon as the translation stage moves towards the inspection position under the microscope, the lever 13 is released and the arm 11 is biased to the locating and clamping position with the slide located and clamped by the abutments 10, 15 and 16, as illustrated in FIG. 3.

It will be appreciated that the slide holder 6 is able to be used manually with the operator moving the lever 13 by hand. When the lever 13 is released, it operates to locate and clamp the slide 19 in the required position whereby the need for manual positioning of the slide, other than rough positioning on the slide holder, is not required.

The above described slide holder has a number of important advantages, including the following:

1. The slide holder is designed to permit gross misalignment of a slide as it is positioned on the slide holder by the transfer mechanism.

2. The slide holder operates to position the slide accurately and repetitively, which enables a particular slide to be re-scanned to locate important features at a future time.

3. When the slide holder is operated in the automatic mode, the possibility of slide damage occurring during positioning and clamping of the slide in the slide holder is minimised by the slow movement of the clamping device which is determined by the speed of the motorised translation stage, as well as by the cushioning effect of the spring 17.

4. The slide holder can be used as a stand-alone slide holder for manual slide loading, as well as part of an automatic slide loading mechanism.

5. The slide holder provides a single mechanism designed to perform both the slide positioning and clamping operations.

The slide loader is a stand alone system which does not require an in-built microscope, and is capable of loading and unloading slides from a number of different optical microscopes equipped with motorised translation stages.

The invention claimed is:

1. An automated microscope slide loading apparatus comprising:
    a slide holder comprising slide clamping and locating means including a clamping arm with slide engaging abutments and having an open position for loading and unloading a slide and a closed position for clamping a slide into a fixed position on the holder for inspection or scanning by a microscope wherein,
    the clamping and locating means further comprises engagement means remote from the clamping arm for engagement with a slide loader such that the clamping arm is moved from the closed position to the open position during movement of the slide holder away from an inspection or scanning position of the slide holder under a microscope to a slide loading and unloading position of the slide holder at a distance from the microscope.

2. An automated microscope slide loading apparatus as defined in claim 1, wherein the slide loader further comprises a housing for a plurality of slide supporting trays; and transfer means for automated transfer of slides to and from a selected tray and the slide holder.

3. An automated microscope slide loading apparatus as defined in claim 2, wherein the transfer means is mounted within the slide loader for independent horizontal and vertical movements during slide transfer to and from the selected tray and the slide holder.

4. An automated microscope slide loading apparatus as defined in claim 3, wherein the transfer means includes a robot head moved in response to a command for enabling automated lifting of slides from the selected tray and depositing of slides on the slide holder.

5. An automated microscope slide loading apparatus as defined in claim 2 wherein the transfer means includes a barcode reader for reading a bar code applied in relation to each of the slides thereby enabling the slide loader to identify and track slides to ensure that the slides are monitored and validated as they are transferred to and from a selected tray and slide holder.

6. An automated microscope slide loading apparatus as defined in claim 5, wherein the transfer means includes a robot head moved in response to a command for enabling automated lifting of slides from the selected tray and depositing of slides on the slide holder, and wherein the barcode reader is supported by and moves with the robot head.

* * * * *